Figure 1:
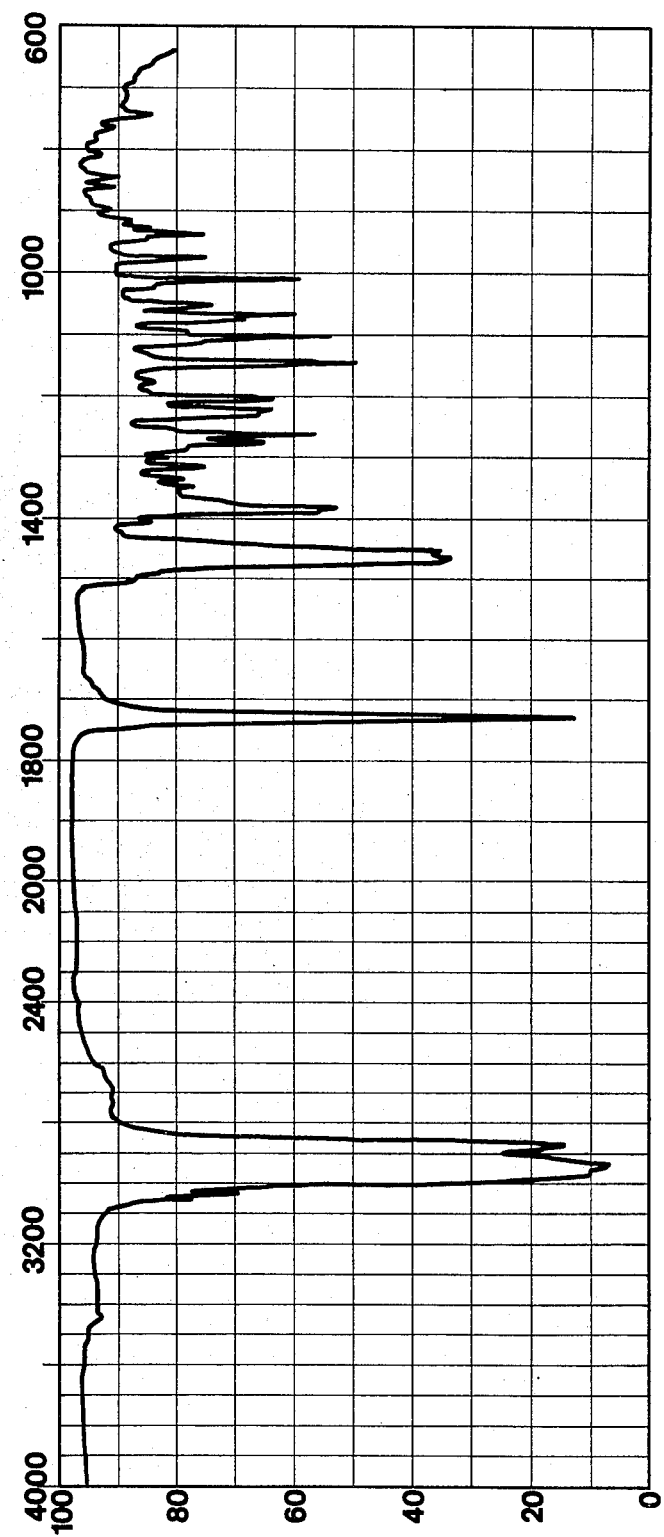

United States Patent [19]

Bernareggi et al.

[11] 4,411,902
[45] Oct. 25, 1983

[54] SALTS OF ENDO-8-METHYL-8-SYN-ALKYL-8-AZONIABICYCLO-[3.2.1]-OCTANE-3-ALKYLCARBOXYLATES, AND THERAPEUTIC COMPOSITIONS CONTAINING THEM

[75] Inventors: Virgilio Bernareggi, Cologno Monzese; Roberto Margutti, Milan; Fausto Bonifacio, Milan; Maurizio Fano, Bresso, all of Italy

[73] Assignee: Valeas S.p.A., Milan, Italy

[21] Appl. No.: 270,008

[22] Filed: Jun. 3, 1981

[30] Foreign Application Priority Data

Jun. 18, 1980 [IT] Italy .................... 22843 A/80

[51] Int. Cl.³ .................... C07D 451/10; A61K 31/46
[52] U.S. Cl. ......................... 424/265; 546/129
[58] Field of Search ............... 546/129; 424/265

[56] References Cited

U.S. PATENT DOCUMENTS 2,962,499 11/1960 Weiner et al. .................... 546/129
3,170,927 2/1965 Nador et al. .................... 546/129

Primary Examiner—Alan L. Rotman
Attorney, Agent, or Firm—Stevens, Davis, Miller & Mosher

[57] ABSTRACT

The invention relates to new salts of endo-8-methyl-8-syn-alkyl-8-azoniabicyclo-[3.2.1]-octane-3-alkylcarboxylates, of formula:

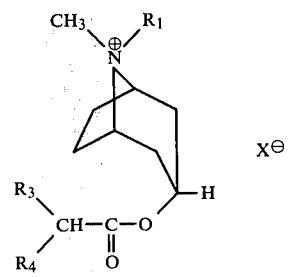

in which $R_1$ is a linear or branched alkyl radical of 2–5 C atoms, a cycloalkyl radical of 3–6 C atoms, or a phenyl-alkyl radical, $R_3$ and $R_4$, which can be the same or different, are alkyl radicals of 1–6 C atoms, X is a halide ion.

The new compounds are potent spasmolytics.

5 Claims, 4 Drawing Figures

SALTS OF ENDO-8-METHYL-8-SYN-ALKYL-8-AZONIABICYCLO-[3.2.1]-OCTANE-3-ALKYLCARBOXYLATES, AND THERAPEUTIC COMPOSITIONS CONTAINING THEM

This invention relates to a new class of salts of endo-8-methyl-8-syn-alkyl-8-azoniabicyclo-[3.2.1]-octane-3-alkylcarboxylates, of formula:

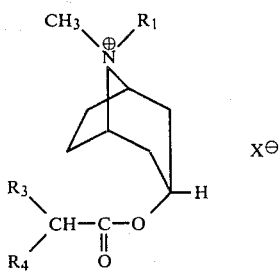
(1)

in which:

$R_1$ is a linear or branched alkyl radical of 2–5 C atoms, a cycloalkyl radical of 3–6 C atoms, or a phenyl-alkyl radical $R_3$ and $R_4$, which can be the same or different, are alkyl radicals of 1–6 C atoms X is a halide ion.

The denomination 8-syn-alkyl relates to and defines the position with the alkyl radical Rhd 1 with respect to the N atom in position 8, whereas the endo-8-methyl-8-anti-alkyl8-azoniabicyclo-[3.2.1]-octane3-alkylcarboxylates are compounds of general formula:

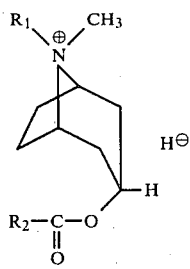
(2)

These latter compounds (2) of the endo-anti series are referred to in U.S. Pat. No. 2,962,499, which describes and claims a class of esters of tropine (endo-8-methyl-8-azabicyclo-3.2.1]-octan-3-ol), attributing to them the two following general formulas (3) and (4) without distincition:

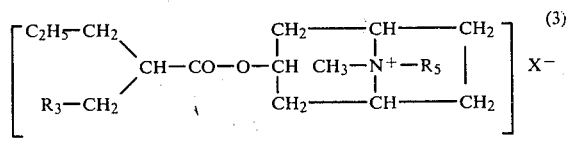
(3)

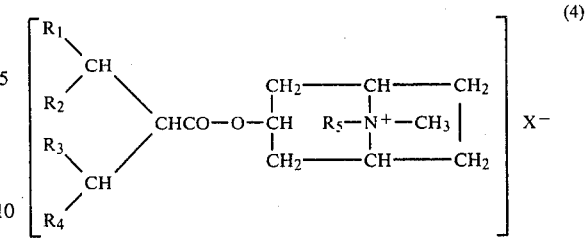
(4)

Although this patent gives no information regarding the spacial structure of the prepared compounds, this can be determined with certainty on the basis of the described preparation process, starting from tropine, by esterifying the hydroxyl with acid chlorides followed by quaternisation of the nitrogen with alkyl halides.

In this respect, according to the general rule determined by Fodor in 1955 (Fodor et al.; Acta Chim. Acad. Sci. Hung. 5, 379–1955), during quaternisation of compounds of the tropane (8-alkyl-8-azabicyclo-[3.2.1]-octane) series, the radical introduced becomes positioned above the pyrrolidine ring, whereas the alkyl group already present on the nitrogen moves above the piperidine ring. Consequently, by applying this rule to the case of U.S. Pat. No. 2,962,499, it can be certain that the synthesis process used gives rise to the following series of reactions:

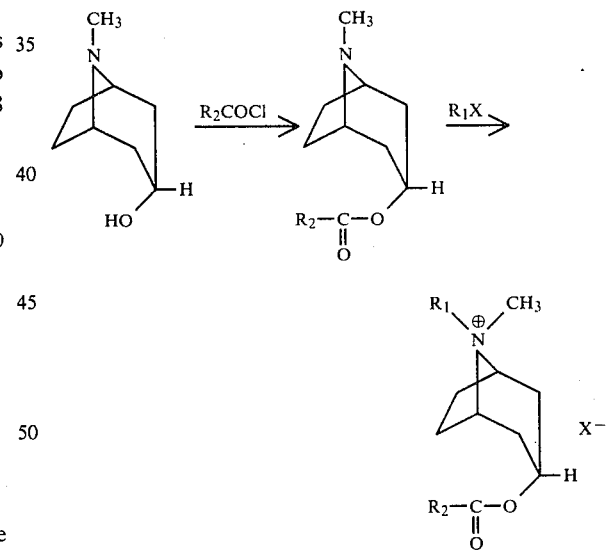

which leads to endo-8-methyl-8-anti-alkyl-8-azoniabicyclo-[3.2.1]-octane-3-alkylcarboxylates, i.e. to the formation of compounds which are position isomers of the compounds of formula (1).

Compounds of formula (1) have however never been prepared up to the present time. The preparation process for the compounds of formula (1), which also forms part of the present invention, is characterised by the quaternisation of endo-8-alkyl-8-azabicyclo:[3.2.1]-octan-3-ol esters with methyl halides, according to the scheme:

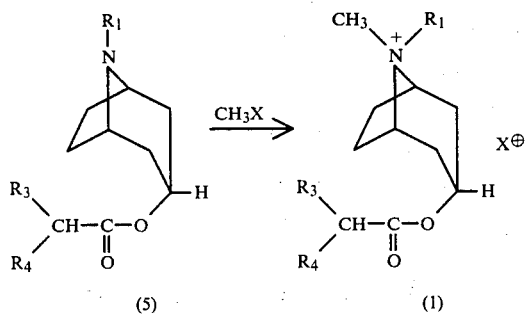

in which $R_1$, $R_3$ and $R_4$ are as heretofore defined.

Such a process ensures the preparation of (endo, syn) compounds according to the present invention, which are quire distinct both from the chemico-physical property aspect and from the pharmacological property aspect from the corresponding (endo, anti) compounds, as will be demonstrated hereinafter. Said quaternisation reaction is preferably carried out by treating the endo-8-alkyl-8-azabicyclo-[3.2.1]-octan-3-ol ester with a large excess of methyl halide in an organic solvent at ambient temperature. Suitable solvents are methylene chloride, chloroform and acetonitrile. The compounds of formula (5), which are the essential intermediate for carrying out the process according to the invention, can be prepared by various alternative methods described schematically hereinafter:

(A) Stereo-selective hydrogenation of 8-alkyl-8-azabicyclo-[3.2.1]-octan-3-ones with Raney Ni to the corresponding endo-8-alkyl-8-azabicyclo-[3.2.1]-octan-3-ols, and esterification of the hydroxyl with acylating compounds. The operational stages are indicated by the following reaction schemes:

$a_1$ - Reduction

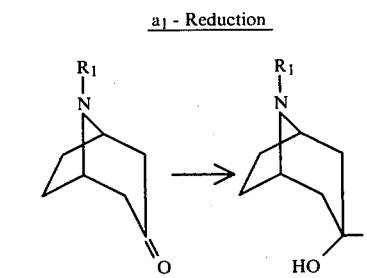

$a_2$ - Esterification

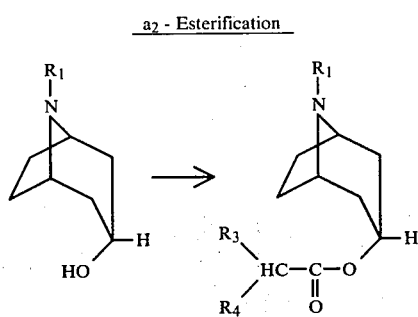

The initial 8-alkyl-8-azabicyclo-[3.2.1]-octan-3ones are prepared by the Robinson-Schöpf method (Schöpf et al.: J. Lieb. Ann der Chemie, 518, 1, 1935) from 2,5-dimethoxy-tetrahydrofuran, acetone-dicarboxylic acid and a primary amine.

Stage ($a_1$) is preferably carried out in a polar organic solvent such as methyl or ethyl alcohol. Stage ($a_2$) can be carried out using a suitable derivative of the required acid as the acylating agent. Preferably the acid chloride is used, and is reacted directly with the endo-8-alkyl-8-azabicyclo-[3.2.1]- -octan-3-ol-hydrochloride. The acid chloride can be also reacted with the endo-8-alkyl-8-azabicyclo-[3.2.1]-octan-3-ol in the presence of a suitable organic base which also acts as a solvent, preferably pyridine or triethylamine. The acylation is preferably carried out at a temperature of between 50° and the reflux temperature of the mixture.

(B) By treating endo-8-methyl-8-azabicyclo-[3.2.1]-octane-3-acetate with demethylating agents, alkylating the compound thus obtained with alkyl halides to give the corresponding endo-8-alkyl-8-azabicyclo-[3.2.1]- -octane-3-acetates, saponifying the acetyl group, and esterifying the free hydroxide with the desired acyl derivative. The operational stages according to this process are represented by the following reaction schemes:

$b_1$ - Demethylation

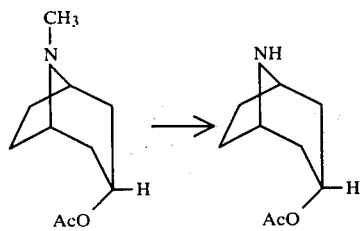

$b_2$ - Alkylation

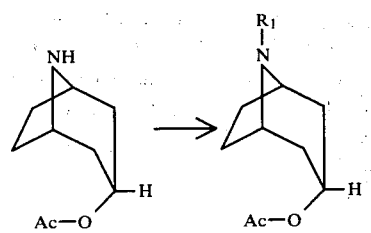

$b_3$ - Saponification

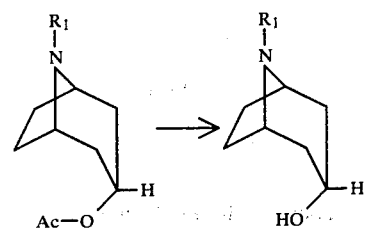

$b_4$ - Esterification

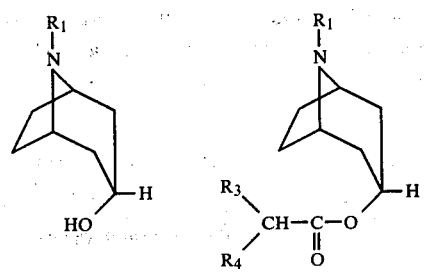

The endo-8-methyl-8-azabicyclo-[3.2.1]-octane-3-acetate, which represents the starting substance for this synthesis, is prepared by acetylating endo-8-methyl-8-azabicyclo-[3.2.1]-octan-3-ol by the normal acetylation methods such as reaction with acetyl chloride in toluene or treatment with boiling acetic anhydride.

Stage ($b_1$) can be carried out with demethylating agents such as phosgene or 2,2,2-trichloroethylchloroformate. It is preferably carried out with phosgene in an organic solvent such as toluene at a temperature of $-50°/0°$ C. Stage ($b_2$) is carried out by reacting the endo-8-azabicyclo-[3.2.1]-octane-3-acetate with alkylating agents of formula $R_1X$, in which X is a halogen, preferably in the presence of an inert organic solvent such as acetonitrile or methylene chloride at a temperature of $50°/100°$ C. The saponification stage ($b_3$) is carried out preferably with strong alkalis in an alcoholic solution. The esterification stage ($b_4$) can be carried out under the same conditions as described for the preceding point ($a_2$).

(C) By esterification of endo-8-methyl-8-azabicyclo-[3.2.1]-octan-3-ol to the corresponding ester containing the required acid radical, demethylation of the ester obtained, and alkylation of the nor-derivative. The operational stages in this process are represented by the following reaction schemes:

$c_1$ - Esterification

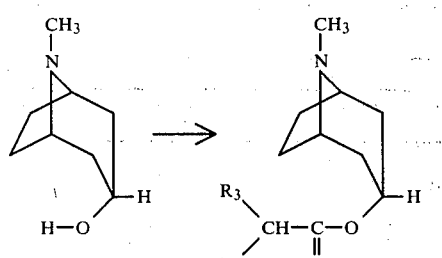

$c_2$ - Demethylation

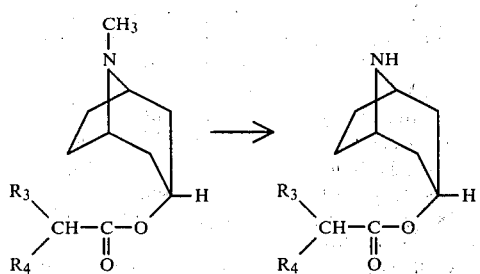

$c_3$ - Alkylation

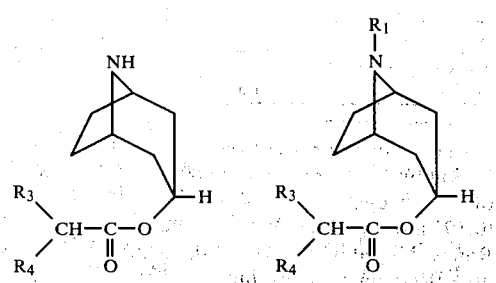

The esterification stage ($c_1$) is carried out by reacting the endo-8-methyl-8-azabicyclo-[3.2.1]-octan-3-ol with an acylating agent under the same conditions as described under the preceding point ($a_2$). The demethylation stage ($c_2$) can be carried out by demethylating agents such as phosgene or 2,2,2-trichloroethylchloroformate under the same conditions as described under the preceding point ($b_1$). The nor-derivative alkylation stage ($c_3$) is carried out with an alkylating agent of formula $R_1X$ under the same conditions as described under the preceding point ($b_2$).

Some examples of preparation of the new compounds according to the invention are described hereinafter in order to illustrate certain preferred methods of carrying out the invention process. On the basis of the description given, all possible modifications, these being included within the scope of the invention, are immediately apparent to the expert of the art.

EXAMPLE 1 - Process for preparing endo-8-methyl-8-syn-ethyl-8-azoniabicyclo-[3.2.1]-octane-3-(2-propyl)-pentanoate bromide (Method A)

8-ethyl-8-azabicyclo-[3.2.1]-octan-3-one:

52 ml of 2,5-dimethoxy-tetrahydrofuran (0.402 moles) are dissolved in 58 ml of water and acidified with 1.2 ml of 37% hydrochloric acid. After 15 minutes, 58 g of acetonedicarboxylic acid (0.397 moles) are added followed by 40.4 g of tribasic sodium citrate bihydrate (0.137 moles) dissolved in 58 ml of water. 18.5 g of ethylamine (0.411 moles) in 35 ml of water are then dripped in. The mixture is left stirring until carbon dioxide ceases to be evolved. It is then saturated with $K_2CO_3$ and extracted with ethyl ether. After drying and evaporating the solvent, the crude product is distilled under vacuum. 27.9 g of 8-ethyl-8-azabicyclo-[3.2.1]-octan-3-one are obtained.

Yield: 46% with respect to the acetone dicarboxylic acid; boiling point: 96–102° C. at 9 mmHg.

| | % | C | H | N |
|---|---|---|---|---|
| Analysis for $C_9H_{15}NO$ | Calculated | 70.50 | 9.87 | 9.14 |
| | Found | 70.44 | 9.76 | 9.13 |

Endo-8-ethyl-8-azabicyclo-[2.3.1]-octan-3-ol:

26 g of 8-ethyl-8-azabicyclo-[3.2.1]-octan-3-one (0.170 moles) are dissolved in 26 ml of ethyl alcohol to which about 4 g of Raney Ni catalyst have been added, and the mixture is hydrogenated. On termination, the catalyst is filtered off, the solvent is evaporated and the residue crystallised with acetone. 22.4 g of endo-8-ethyl-8-azabicyclo-[3.2.1]-octan-3-ol are obtained.

Yield: 85%; melting point: 77–79° C.

| | % | C | H | N |
|---|---|---|---|---|
| Analysis for $C_9H_{17}NO$ | Calculated | 69.63 | 11.04 | 9.02 |
| | Found | 69.51 | 11.03 | 9.06 |

Endo-8-ethyl-8-azabicyclo-[3.2.1]-octane-3-2-propyl)-pentanoate:

20 g of endo-8-ethyl-8-azabicyclo-[3.2.1]-octan-3-ol (0.129 moles) are suspended in 130 ml of pyridine, and 23 g of dipropyl-acetyl-chloride (0.142 moles) are added under stirring. After four hours under reflux, the pyridine is washed with 5% HCl, dried and evaporated to dryness. The solid residue is crystallised with 1:3 chloroform-n.hexane (v/v), then dissolved in water, made basic and extracted with ether. After drying, the organic phase is evaported to dryness. 23.56 g of endo-8- ethyl-8-azabicyclo-[3.2.1]-octane-3-(2-propyl)-pentanoate are obtained.

Yield: 65%; acidimetric titre: 98.9%.

| % | | C | H | N |
|---|---|---|---|---|
| Analysis for $C_{17}H_{31}NO_2$ | Calculated: | 72.53 | 11.11 | 4.98 |
| | Found: | 72.38 | 10.90 | 4.95 |

Endo-8-methyl-8-syn-ethyl-8-azoniabicyclo-[3.2.1]-octane-3-(2-propyl)-pentanoate bromide:

22 g of endo-8-ethyl-8-azabicyclo-[3.2.1]-octane-3-(2-propyl)-pentanoate (0.078 moles) are dissolved in 165 ml of methylene chloride. 16 g of $CH_3Br$ (0.17 moles) are absorbed into the solution, and the reactor is left at ambient temperature for three days. The precipitate formed is diluted with 165 ml of ethyl ether and filtered.

27.3 g of endo-8-methyl-8-syn-ethyl-8-azoniabicyclo-[3.2.1]-octane-3-(2-propyl)-pentanoate bromide are obtained.

Yield: 93%; melting point: $\geq$ 302° C. (decomposed).

| % | | C | H | N |
|---|---|---|---|---|
| Analysis for $C_{18}H_{34}BrNO_2$ | Calculated: | 57.40 | 9.12 | 3.72 |
| | Found: | 57.38 | 9.21 | 3.79 |

$Br^\ominus$ : 99.7%.

EXAMPLE 2 - Process for preparing endo-8-methyl-8-sny-(1-methyl)-ethyl-8-azoniabicyclo-[3.2.1]-octane-3-(2-propyl)-pentanoate bromide (val 4000) (Method A).

8-(1-methyl)-ethyl-8-azabicyclo-[3.2.1]-octan-3-one:

Following the procedure described in example 1, 45 ml of 2,5-dimethoxytetrahydrofuran (0.348 moles) in 50 ml of water and 0.1 ml of HCl are reacted with 50 g of acetone dicarboxylic acid (0.342 moles) and 35 g of tribasic sodium citrate bihydrate (0.119 moles) in 50 ml of water, 20 g of ice and 30 ml of isopropylamine (0.356) to give the required product. 23 g of 8-(1-methyl)-ethyl-8-azabicyclo-[3.2.1]-octan-3-one are obtained.

Yield: 40% with respect to the acetonedicarboxylic acid;

boiling point: 75–80° C. at 2 mmHg.

| % | | C | H | N |
|---|---|---|---|---|
| Analysis for $C_{10}H_{17}NO$ | Calculated: | 71.81 | 10.25 | 8.37 |
| | Found: | 70.99 | 10.08 | 8.33 |

Endo-8-(1-methyl)-ethyl-8-azabicyclo-[3.2.1]-octan-3-ol:

Following the procedure described in example 1, 20 g of 8-(1-methyl)-ethyl-8-azabicyclo-[3.2.1]-octan-3-one (0.120 moles) dissolved in 20 ml of ethanol and to which about 9 g of Raney Ni catalyst were added are hydrogenated to give the require product.

19 g of endo-8-(1-methyl)-ethyl-8-azabicyclo-[3.2.1]-octan-3-ol are obtained.

Yield: 94%; melting point: 105°–107° C.

| % | | C | H | N |
|---|---|---|---|---|
| Analysis for $C_{10}H_{19}NO$ | Calculated: | 70.95 | 11.31 | 8.28 |
| | Found: | 70.68 | 10.99 | 8.11 |

Endo-8-(1-methyl)-ethyl-8-azabicyclo-[3.2.1]-octane-3-(2-propyl)-pentanoate:

Following the procedure described in example 1, 18 g of endo-8-(1-methyl)-ethyl-8-azabicyclo-[3.2.1]-octan-3-ol (0.106 moles) in 115 ml of pyridine are reacted with 19 g of dipropyl-acetylchloride (0.117) to give the required product.

22.3 g of endo-8-(1-methyl)-ethyl-8-azabicyclo-[3.2.1]-octane-3-(2-propyl)-pentanoate are obtained.

Yield: 70%; acidimetric titre: 100.2%.

| % | | C | H | N |
|---|---|---|---|---|
| Analysis for $C_{18}H_{33}NO_2$ | Calculated: | 73.15 | 11.26 | 4.74 |
| | Found: | 72.98 | 11.29 | 4.69 |

Endo-8-methyl-8-syn-(1-methyl)-ethyl-8-azoniabicyclo-[3.2.1]-octane-3-(2-propyl)-pentanoate bromide (VAL 4000).

Following the procedure described in the example, 1.20 g of endo-8-(1-methyl)-ethyl-8-azabicyclo-[3.2.1]-octane-3-(2-propyl)-pentanoate (0.068 moles) in 150 ml of methylene chloride are reacted with 14 g of $CH_3Br$ (0.147 moles) and, after two days, diluted with 150 ml of ethyl ether and filtered to give the required product.

25.6 g of endo-8-methyl-8-syn-(1-methyl)-ethyl-8-azoniabicyclo-[3.2.1]-octane-3-(2-propyl)-pentanoate bromide are obtained.

Yield: 97%; melting point: >280° C. (decomposed).

| % | | C | H | N |
|---|---|---|---|---|
| Analysis for $C_{19}H_{36}BrNO_2$ | Calculated: | 58.42 | 9.29 | 3.59 |
| | Found: | 58.55 | 8.32 | 3.49 |

$Br^\ominus$: 101%.

EXAMPLE 3

Process for preparing endo-8-methyl-8-syn-cyclopropyl-8-azoniabicyclo-[3.2.1]-octane-3-(2-propyl)-pentanoate bromide.

8-cyclopropyl-8-azoniabicyclo-[3.2.1]-octan-3-one:

Following the procedure described in example 1, 68 ml of 2,5-dimethoxy-tetrahydrofuran (0.525 moles) in 75 ml of water and 0.15 ml of HCl are reacted with 75 g of acetonedicarboxylic acid (0.514 moles), 52.2 g of tribasic sodium citrate bihydrate (0.178 moles) in 75 ml of water, 30 g of ice and 30.6 g of cyclopropylamine (0.537 moles) to give the required product.

28 g of 8-cyclopropyl-8-azabicyclo-[3.2.1]-octan-3-one are obtained.

Yield: 33% with respect to the acetonedicarboxylic acid; boiling point: 60°–70° C. at 2 mmHg.

| % | | C | H | N |
|---|---|---|---|---|
| Analysis for $C_{10}H_{15}NO$ | Calculated: | 72.69 | 9.15 | 8.48 |
| | Found: | 70.93 | 9.51 | 8.62 |

Endo-8-cyclopropyl-8-azabicyclo-[3.2.1]-octan-3-ol:

Following the procedure described in example 1, 26 g of 8-cyclopropyl-8-azabicyclo-[3.2.1]-octan-3-one (0.157 moles) in 30 ml of ethanol to which about 4 g of Raney Ni catalyst were added, are hydrogenated to give the required product.

18.5 g of endo-8-cyclopropyl-8-azabicyclo-[3.2.1]-octan-3-ol are obtained. Yield: 70%; melting point: 172° C.

| % | C | H | N |
|---|---|---|---|
| Analysis for C$_{10}$H$_{17}$NO Calculated: | 71.81 | 10.25 | 8.37 |
| Found: | 71.60 | 10.13 | 8.21 |

Endo-8-cyclopropyl-8-azabicyclo-[3.2.1]-octane-3-(2-propyl)-pentanoate:

Following the procedure described in example 1, 16.5 g of endo-8-cyclopropyl-8-azabicyclo-[3.2.1]-octan-3-ol (0.099 moles) in 105 ml of pyridine are reacted with 17.7 g of dipropyl-acetylchloride (0.109 moles) to give the required product:

15.9 g of endo-8-cyclopropyl-8-azabicyclo-[3.2.1]-octane-3-(2-propyl)-pentanoate are obtained.

Yield: 55%; acidimetric titre: 98.8%

| % | C | H | N |
|---|---|---|---|
| Analysis for C$_{18}$H$_{31}$NO$_2$ Calculated: | 73.65 | 10.65 | 4.78 |
| Found: | 73.58 | 10.57 | 4.62 |

Endo-8-methyl-8-syn-cyclopropyl-8-azoniabicyclo-[3.2.1]-octane-3-(2-propyl)-pentanoate bromide.

Following the procedure described in example 1, 13 g of endo-8-cyclopropyl-8-azabicyclo-[3.2.1]-octane-3-(2-propyl)-pentanoate (0.044 moles) in 100 ml of methylene chloride are reacted with 10.5 g of CH$_3$Br (0.110 moles) to give the required product. 15.5 g of endo-8-methyl-8-syn-cyclopropyl-8-azoniabicyclo-[3.2.1]-octane-3-(2-propyl)-pentanoate bromide are obtained.

Yield: 91%; melting point: ≧282° C. (decomposed).

| % | C | H | N |
|---|---|---|---|
| Analysis for C$_{19}$H$_{34}$BrNO$_2$ Calculated: | 58.72 | 8.83 | 3.61 |
| Found: | 58.90 | 8.77 | 3.55 |

Br$^\ominus$:99.8%.

EXAMPLE 4

Process for preparing endo-8-methyl-8-syn-benzyl-8-azoniabicyclo-[3.2.1]-octane-3-(2-propyl)-pentanoate bromide (Method A).

8-benzyl-8-azabicyclo-[3.2.1]-octan-3-one:

Following the procedure described in example 1, 57 ml of 2.5-dimethoxy-tetrahydrofuran (0.440 moles) in 64 ml of water and 0.12 ml of HCl are reacted with 62.9 g of acetonedicarboxylic acid (0.431 moles), 44 g of tribasic sodium citrate bihydrate (0.149 moles) in 64 ml of water, 25 g of ice and 48.15 g of benzylamine (0.450 moles) to give the required product.

41 g of 8-benzyl-8-azabicyclo-[3.2.1]-octan-3-one are obtained.

Yield: 44% with respect to the acetonedicarboxylic acid; boiling point: 135°-140° C. at 0.5 mmHg.

| % | C | H | N |
|---|---|---|---|
| Analysis for C$_{14}$H$_{17}$NO Calculated: | 78.10 | 7.96 | 6.51 |
| Found: | 77.94 | 7.83 | 6.41 |

Endo-8-benzyl-8-azabicyclo-[3.2.1]-octan-3-ol:

Following the procedure described in example 1, 39 g of 8-benzyl-8-azabicyclo-[3.2.1]-octan-3-one (0.181 moles) in 50 ml of ethanol, to which about 5 g of Raney Ni catalyst were added, are hydrogenated to give the required product.

30.2 g of endo-8-benzyl-8-azabicyclo-[3.2.1]-octan-3-ol are obtained.

Yield: 77%; melting point: 90°-91°0 C.

| % | C | H | N |
|---|---|---|---|
| Analysis for C$_{14}$H$_{19}$NO Calculated: | 77.38 | 8.81 | 6.45 |
| Found: | 77.33 | 8.85 | 6.58 |

Endo-8-benzyl-8-azabicyclo-[3.2.1]-octane-3-(2-propyl)-pentanoate:

Following the procedure described in Example 1, 28 g of endo-8-benzyl-8-azabicyclo-[3.2.1]-octan-3-ol (0.129 moles) in 160 ml of pyridine are reacted with 23 g of dipropyl-acetylchloride (0.142 moles) to give the required product.

30 g of endo-8-benzyl-8-azabicyclo-[3.2.1]-octane-3-(2-propyl)-pentanoate are obtained.

Yield: 68%; acidimetric titre: 98.95%.

| % | C | H | N |
|---|---|---|---|
| Analysis for C$_{22}$H$_{33}$NO$_2$ Calculated: | 76.91 | 9.69 | 9.32 |
| Found: | 76.55 | 9.76 | 9.25 |

Endo-8-methyl-8-syn-benzyl-8-azoniabicyclo-[3.2.1]-octane-3-(2-propyl)-pentanoate bromide.

Following the procedure described in example 1, 28 g of endo-8-benzyl-8-azabicyclo-[3.2.1]-octane-3-(2-propyl)-pentanoate (0.082) in 210 ml of methylene chloride are reacted with 19.5 g of CH$_3$Br (0.205 moles) to give the required product.

31.6 g of endo-8-methyl-8-syn-benzyl-8-azoniabicyclo-[3.2.1]-octane-3-(2-propyl)-pentanoate bromide are obtained.

Yield: 88%; melting point: ≧260° C. (decomposed).

| % | C | H | N |
|---|---|---|---|
| Analysis for C$_{23}$H$_{36}$BrNO Calculated | 62.97 | 8.28 | 3.20 |
| Found | 62.00 | 8.22 | 3.16 |

Br$^\ominus$: 98.7%

EXAMPLE 5

Process for preparing endo-8-methyl-8-syn-(1-methyl)-ethyl-8-azoniabicyclo-[3.2.1]-octane-3-(2-propyl)-pentanoate bromide (Method B)

Endo-8-azabicyclo-[3.2.1]-octane-3-acetate:

12 g of phosgene (0.122 moles) in a 20% solution in toluene cooled to −50° are added to 15 g of endo-8-methyl-8-azabicyclo-[3.2.1]-octane-3-acetate (0.082 moles) in 15 ml of anhydrous toluene. After 30 minutes the cooling is removed, and after 4 hours nitrogen is blown in for 15 minutes.

The solution is then extracted with water, dried and evaporated to dryness.

The residue is dissolved in water and heated to 60° C. for 2 hours, the clear solution is then washed with ether, made basic with ammonia and extracted with chloroform. After drying, the solvent is evaporated to give the required product. 10.4 g of endo-8-azabicyclo-[3.2.1]-octane-3-acetate are obtained.

Yield: 75%; oxalate: melting point 176°-178° C.

| % | C | H | N |
|---|---|---|---|
| Analysis for C$_9$H$_{15}$NO$_2$ Calculated | 63.86 | 8.94 | 8.28 |

| % | C | H | N |
|---|---|---|---|
| Found | 63.92 | 8.98 | 8.19 |

Endo-8-(1-methyl)-ethyl-8-azabicyclo-[3.2.1]-octan-3-ol:

9 g of endo-8-azabicyclo-[3.2.1]-octane-3-acetate (0.053 moles) in 20 ml of acetonitrile, to which 7.2 g of isopropyl bromide (0.058 moles) and 5.6 g of $Na_2CO_3$ (0.053 moles) are added, are heated to 50° C. for 24 hours and are then washed with 3×10 ml of water, dried and evaporated to dryness.

The crude residue is dissolved in 50 ml of 10% alcoholic KOH, and heated under reflux for 2 hours. The solution is then evaporated to dryness, and the residue is dissolved in a 1:1 mixture of water and ethyl ether. After separation, the organic phase is dried and evaporated to dryness to give the required product. 6 g of endo-8-(1-methyl)-ethyl-8-azabicyclo-[3.2.1]-octan-3-ol are obtained.

Yield: 66%; melting point: 105°–107° C.

| | % | C | H | N |
|---|---|---|---|---|
| Analysis for $C_{10}H_{19}NO$ | Calculated | 70.95 | 11.31 | 8.28 |
| | Found | 70.68 | 10.99 | 8.11 |

Endo-8-(1-methyl)-ethyl-8-azoniabicyclo-[3.2.1]-octan-3-ol chloride:

50 g of endo-8-(1-methyl)-ethyl-8-azabicyclo-[3.2.1]-octan-3-ol (0.296 moles) are dissolved in 200 ml of anhydrous ethanol and acidified to pH 3 with hydrochloric acid gas. The precipitate formed is diluted with 1000 ml of anhydrous ethyl ether and filtered to give the required product.

55 g of endo-8-(1-methyl)-ethyl-8-azoniabicyclo-[3.2.1]-octan-3-ol chloride are obtained.

Yield: 95.8%, melting point: ≧280° C. (decomposed).

| | % | C | H | N |
|---|---|---|---|---|
| Analysis for $C_{10}H_{20}ClNO$ | Calculated | 58.35 | 9.80 | 6.81 |
| | Found | 58.22 | 9.78 | 6.90 |

Endo-8-(1-methyl)-ethyl-8-azabicyclo-[3.2.1]-octane-3-(2-propyl)-pentanoate:

48 g of endo-8-(1-methyl)-ethyl-8-azoniabicyclo-[3.2.1]-octan-3-ol chloride (0.236 moles) are heated under stirring to 70° C., and 40.28 g of dipropyl-acetylchloride (0.248 moles) are then dripped in. The mixture is heated to 80° C. for 2 hours, then after cooling is dissolved in 250 ml of water, washed with benzene, made basic with $K_2CO_3$ and extracted with methylene chloride, the extract then being dried and evaporated to give the required product.

75 g of endo-8-(1-methyl)-ethyl-8-azabicyclo-[3.2.1]-octane-3-(2-propyl)-pentanoate are obtained.

Yield: 82%; acidimetric titre: 99.5%.

| | % | C | H | N |
|---|---|---|---|---|
| Analysis for $C_{18}H_{33}NO_2$ | Calculated | 73.15 | 11.26 | 4.74 |
| | Found | 73.10 | 11.19 | 4.69 |

The endo-8-(1-methyl)-ethyl-8-azabicyclo-[3.2.1]-octane-3-(2-propyl)-pentanoate obtained in this manner is converted into the corresponding methyl bromide as described in example 2.

EXAMPLE 6

Process for preparing endo-8-methyl-8-syn-butyl-8-azoniabicyclo-[3.2.1]-octane-3-(2-propyl)-pentanoate bromide (Method C)

Endo-8-methyl-8-azoniabicyclo-[3.2.1]-octane-3-(2-propyl)-pentanoate chloride:

46 g of endo-8-methyl-8-azabicyclo-[3.2.1]-octan-3-ol (0.326 moles) in 250 ml of pyridine to which 56 g of dipropyl-acetylchloride (0.345 moles) are added, are reacted under reflux for 6 hours, the pyridine is then evaporated, and the residue is dissolved in chloroform and washed with dilute hydrochloric acid. After drying, the solvent is evaporated and the crude semi-solid is suspended in anhydrous ethyl ether containing 5% of ethanol, and stirred until completely crystallised.

45 g of endo-8-methyl-8-azoniabicyclo-[3.2.1]-octane-3-(2-propyl)-pentanoate chloride are obtained.

Yield: 45%; melting point: 185°–186° C.

| | % | C | H | N |
|---|---|---|---|---|
| Analysis for $C_{16}H_{30}ClNO_2$ | Calculated | 63.21 | 9.95 | 4.61 |
| | Found | 63.15 | 9.89 | 4.54 |

Endo-8-methyl-8-azabicyclo-[3.2.1]-octane-3-(2-propyl)-pentanoate:

42 g of endo-8-methyl-8-azoniabicyclo-[3.2.1]-octane-3-(2-propyl)-pentanoate chloride (0.138 moles) are dissolved in 300 ml of water, made basic with ammonia, and extracted with 3×100 ml of $CH_2Cl_2$. After drying, the solvent is evaporated to give the required product 35.5 g of endo-8-methyl-8-azabicyclo-[3.2.1]-octane-3-(2-propyl)-pentanoate are obtained.

Yield: 96%; acidimetric titre: 98.9%.

| | % | C | H | N |
|---|---|---|---|---|
| Analysis for $C_{16}H_{29}NO_2$ | Calculated | 71.84 | 10.94 | 5.24 |
| | Found | 71.52 | 10.99 | 5.45 |

Endo-8-azabicyclo-[3.2.1]-octane-3-(2-propyl)-pentanoate.

32 g of phosgene (0.325 moles) in a 20% solution in toluene are added, under stirring at −20° C., to 58 g of endo-8-methyl-8-azabicyclo-[3.2.1]-octane-3-(2-propyl)-pentanoate (0.217 moles) dissolved in 130 ml of anhydrous toluene.

The solution is left for 2 days at ambient temperature, the hydrochloride of the unreacted starting substance is removed, and the solvent is distilled off.

The crude residue is dissolved in 100 ml of water and heated to 60° C. under stirring, until $CO_2$ ceases to be evolved.

The clear solution is washed with ethyl ether, then made basic and extracted with methylene chloride. The solvent is then dried and evaporated to give the required product. 39.5 g of endo-8-azabicyclo-[3.2.1]-octane-3-(2-propyl)-pentanoate are obtained.

Yield: 72%; acidimetric titre: 98.6%.

| | % | C | H | N |
|---|---|---|---|---|
| Analysis for $C_{15}H_{27}NO_2$ | Calculated | 71.08 | 10.75 | 5.53 |

-continued

| % | C | H | N |
|---|---|---|---|
| Found | 72.05 | 10.82 | 5.65 |

Endo-8-methyl-8-syn-butyl-8-azoniabicyclo-[3.2.1]-octane-3-(2-propyl)-penetanoate bromide:

35 g of endo-8-azabicyclo-[3.2.1]-octane-3-(2-propyl)-pentanoate (0.138 moles) in 70 ml of acetonitrile, to which 19.86 g of n-butylbromide (0.145 moles) and 14.8 g of $Na_2CO_3$ (0.140 moles) are added, are heated under reflux for 8 hours, then after cooling and filtering the precipitate, the solution is washed with water, dried and evaporated to dryness.

The obtained residue of 23.5 g is dissolved in 120 ml of methylene chloride, and 18 g of $CH_3Br$ (0.190 moles) are added.

28.4 g of endo-8-methyl-8-syn-butyl-8-azoniabicyclo-[3.2.1]-octane-3-(2-propyl)-pentanoate bromide are obtained.

Yield: 51%; melting point: ≧249° C. (decomposed).

| | % | C | H | N |
|---|---|---|---|---|
| Analysis for $C_{20}H_{38}BrNO_2$ | Calculated | 59.36 | 9.47 | 3.46 |
| | Found | 59.82 | 9.51 | 3.49 |

$Br^\ominus$: 98.8%.

EXAMPLE 7 - Process for preparing endo-8-methyl-8-syn-cyclohexyl-8-azoniabicyclo-[3.2.1]-octane-3-(2-propyl)-pentanoate bromide (Method C).

26 g of endo-8-azabicyclo-[3.2.1]-octane-3-(2-propyl)-pentanoate (0.103 moles), prepared according to the procedure described in example 6 and dissolved in 50 ml of acetonitrile, are reacted as described in example 6 with 17.8 g of cyclohexylbromide (0.109 moles) and 11.3 g of $Na_2CO_3$ (0.107 moles), to give the corresponding endo-8-cyclohexyl-8-azabicyclo-[3.2.1]-octane-3-(2-propyl)-pentanoate, which is reacted with 11 g of $CH_3Br$ (0.116 moles) to give the required product.

19 g of endo-8-methyl-8-syn-cyclohexyl-8-azoniabicyclo-[3.2.1]-octane-3-(2-propyl)-pentanoate bromide are obtained.

Yield: 43%; melting point >268° C. (decomposed).

| | % | N | H | N |
|---|---|---|---|---|
| Analysis for $C_{22}H_{40}BrNO_2$ | Calculated: | 61.35 | 9.37 | 3.25 |
| | Found: | 60.85 | 9.28 | 3.42 |

Further endo-8-methyl-8-syn-alkyl-8-azoniabicyclo-[3.2.1]-octane-3-alkyl carboxylate salts were synthesized by one or more processes described in the preceding examples.

Table 1 comprises the main compounds of general formula (1) prepared by the described methods.

TABLE 1

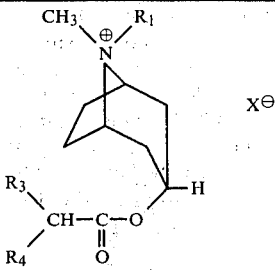

| Compound No. | $R_1$ | $R_3$ | $R_4$ | X | M.P.(°C.)* | C | H | N |
|---|---|---|---|---|---|---|---|---|
| 1 | $C_2H_5$ | $CH_3$ | $CH_3$ | Br | 298 | 52.46 | 8.18 | 4.37 |
| | | | | | | 51.82 | 8.02 | 4.25 |
| 2 | $C_2H_5$ | n-$C_3H_7$ | n-$C_3H_7$ | Br | 302 | 57.40 | 9.12 | 3.72 |
| | | | | | | 57.38 | 9.21 | 3.79 |
| 3 | $C_2H_5$ | n-$C_3H_7$ | n-$C_3H_7$ | I | 330 | 51.03 | 7.93 | 3.24 |
| | | | | | | 50.06 | 7.78 | 3.15 |
| 4 | $C_3H_5$ | n-$C_3H_7$ | n-$C_3H_7$ | Br | 282 | 58.72 | 8.83 | 3.61 |
| | | | | | | 58.90 | 8.77 | 3.55 |
| 5 | i-$C_3H_7$ | $C_2H_5$ | $C_2H_5$ | Br | 262 | 56.31 | 8.90 | 3.87 |
| | | | | | | 55.82 | 8.65 | 3.69 |
| 6 | i-$C_3H_7$ | n-$C_3H_7$ | n-$C_3H_7$ | Br | 281 | 58.42 | 9.29 | 3.59 |
| | | | | | | 58.55 | 9.32 | 3.49 |
| 7 | i-$C_3H_7$ | n-$C_3H_7$ | n-$C_3H_7$ | I | 333 | 52.14 | 8.30 | 3.20 |
| | | | | | | 51.09 | 8.28 | 3.14 |
| 8 | i-$C_3H_7$ | $C_2H_5$ | n-$C_4H_9$ | Br | 259 | 58.42 | 9.29 | 3.59 |
| | | | | | | 58.36 | 9.20 | 3.59 |
| 9 | n-$C_4H_9$ | $C_2H_5$ | $C_2H_5$ | Br | 256 | 57.40 | 9.12 | 3.72 |
| | | | | | | 57.25 | 9.15 | 3.70 |
| 10 | n-$C_4H_9$ | $C_2H_5$ | $C_2H_5$ | I | 336 | 51.03 | 7.93 | 3.24 |
| | | | | | | 51.11 | 8.05 | 3.26 |
| 11 | n-$C_4H_9$ | n-$C_3H_7$ | n-$C_3H_7$ | Br | 249 | 59.36 | 9.47 | 3.46 |
| | | | | | | 59.82 | 9.51 | 3.49 |
| 12 | n-$C_4H_9$ | i-$C_3H_7$ | i-$C_3H_7$ | Br | 258 | 59.36 | 9.47 | 3.46 |
| | | | | | | 59.44 | 9.35 | 3.29 |
| 13 | n-$C_4H_9$ | i-$C_3H_7$ | i-$C_3H_7$ | I | 335 | 53.18 | 8.49 | 3.10 |
| | | | | | | 52.05 | 8.53 | 3.90 |
| 14 | n-$C_4H_9$ | n-$C_3H_7$ | n-$C_4H_9$ | Br | 255 | 60.24 | 9.64 | 3.35 |
| | | | | | | 60.12 | 9.58 | 3.29 |
| 15 | $C_6H_{11}$ | n-$C_3H_7$ | n-$C_3H_7$ | Br | 268 | 61.35 | 9.37 | 3.25 |

TABLE 1-continued

[Structure: bicyclic compound with CH₃ and R₁ on N⊕, X⊖ counterion, and R₃R₄CH-C(=O)-O- ester group]

| Compound No. | R₁ | R₃ | R₄ | X | M.P.(°C.)* | C | H | N |
|---|---|---|---|---|---|---|---|---|
| | | | | | | 60.85 | 9.28 | 3.42 |
| 16 | C₆H₅CH₂ | n-C₂H₅ | n-C₃H₇ | Br | 261 | 67.61 | 6.10 | 2.92 |
| | | | | | | 67.56 | 6.52 | 2.33 |
| 17 | C₆H₅CH₂ | n-C₃H₇ | n-C₃H₇ | Br | 260 | 62.97 | 8.28 | 3.20 |
| | | | | | | 62.00 | 8.22 | 3.16 |
| 18 | C₆H₅CH₂ | n-C₃H₇ | n-C₃H₇ | Cl | 252 | 74.53 | 6.72 | 3.22 |
| | | | | | | 74.45 | 6.61 | 3.16 |

The *M.P. are not corrected.

Although, as previously stated, because of the Fodor rule, the new preparation method followed leads only to the syn structure in the nor-tropane (8-azabicyclo-[3.2.1]-octane) derivatives, this structure was confirmed for the most important compound of those prepared from the applicational viewpoint, by comparing it with the corresponding epimer, prepared in accordance with U.S. Pat. No. 2,962,499.

Endo-8-methyl-8-syn-(1-methyl)-ethyl-8-azoniabicyclo-[3.2.1]-octane-3-(2-propyl)-pentanoate bromide (VAL 4000) prepared according to the given example 2 was compared with endo-8-methyl-8-anti-(1-methyl)-ethyl-8-azoniabicyclo-[3.2.1]-octane-3-(2-propyl)-pentanoate bromide (Endo X) prepared by the process described in example 3 of U.S. Pat. No. 2,962,499.

The physical characteristics of the two products were found to be quite distinct.

BRIEF DESCRIPTION OF DRAWINGS 1-4

In FIG. I and II, the scale 0–100 represents percent transmission and the scale 600–4000 represents frequency; FIG. I represents the I.R. spectra of Val-4000 of the present invention and FIG. II represents the I.R. spectra of Endo-X of the prior art.

Figure 2:
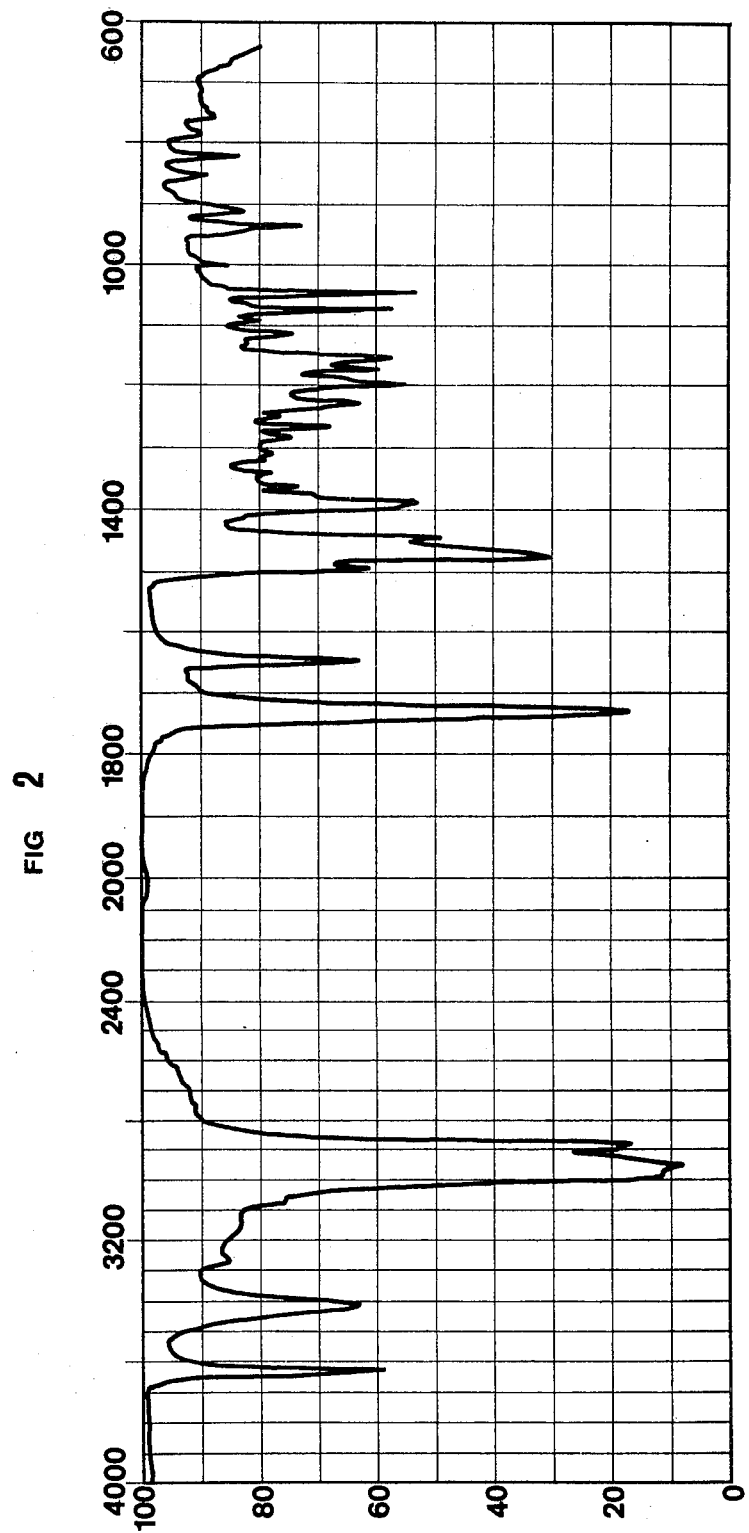
Figure 3:
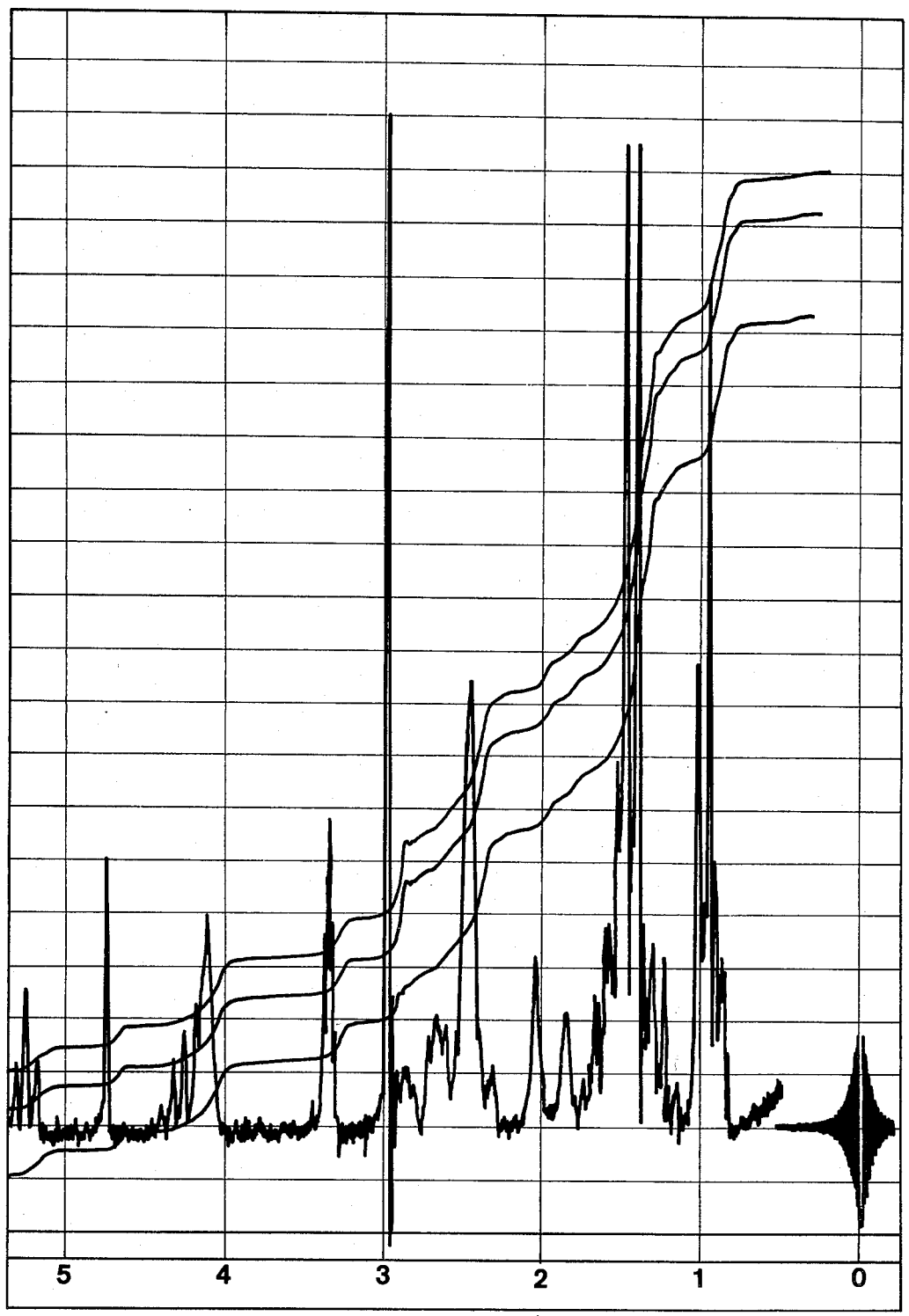
Figure 4:
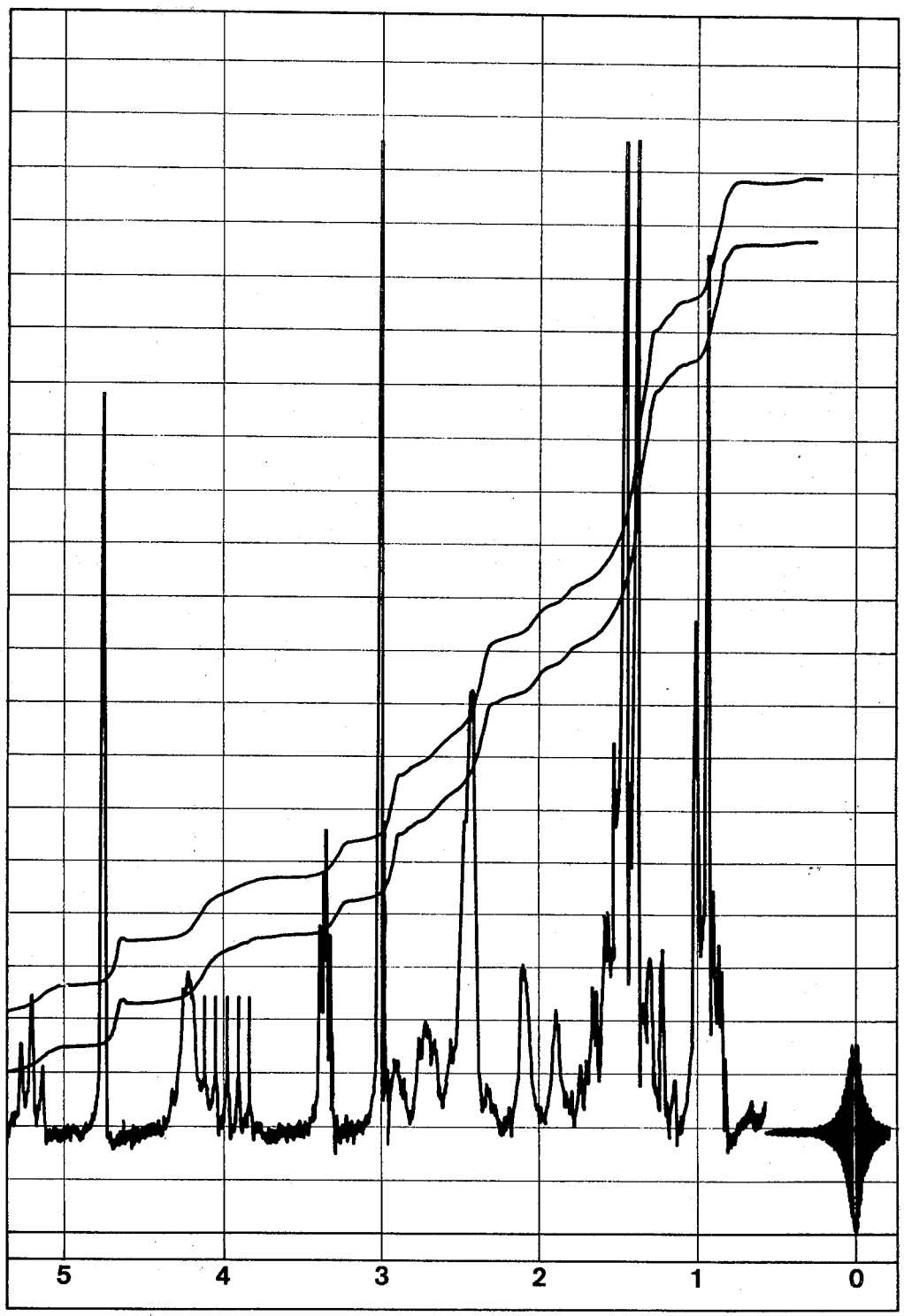

In FIG. III and IV, the scale 0–5 represents delta values and the tall peaks on the graphs represent energy absorption at various cps (cycles per second) values. FIG. III represents N.M.R. spectra for Val-4000 and FIG. IV represents N.M.R. Spectra for Endo-X.
VAL 4000 M.P.=280°–282° C. (decomposed)
Endo X M.P.=264°–266° C. (decomposed)
Infrared spectra in Nujol: attached
  FIG. 1—VAL 4000
  FIG. 2—Endo X
NMR spectra in CD₃OD at 90 M.C.: attached
  FIG. 3—VAL 4000
  FIG. 4—Endo X
VAL 4000
  Chemical shift of the 3-BH of the tropane nucleus=471 cps
  Chemical shift of the isopropyl-CH on the nitrogen=381 cps
  Chemical shift of the -CH₃ on the nitrogen =265 cps
Endo X
  Chemical shift of the 3BH of the tropane nucleus=466 cps
  Chemical shift of the isopropyl -CH on the nitrogen=356 cps
  Chemical shift of the -CH on the nitrogen=269 cps On pharmacological screening, the compounds according to the present invention were found to possess very interesting spasmolytic activity. Table 2 shows by way of example the pA₂ values (Schild H. O., Brit. J. Pharmacol., 2, 189, 1947) of certain compounds pertaining to the described class in comparison with Buscopan (scopolamine-butyl-bromide), a well known spasmolytic, these values being obtained by using the isolated rat ileus prepared by the method of Magnus and coll. (Pflügers Ges. Physiol., 102, 123, 1904), using barium chloride as a contracting agent.

The pA₂ relates to the negative logarithm of the molar antagonist concentration which reduces by 50% the contraction caused by the barium chloride agonist.

Spasmolitic effect of some of the compounds given in table 1 in comparison with Buscopan (scopolamine-butyl-bromide), the spasmolytic effect being evaluated on isolated rat ileus with BaCl₂ and expressed as pA₂. Each pA₂ value is the result of at least six experiments.

TABLE 2

| Compound No. | pA₂ | Reliability limits (p = 0.05) |
|---|---|---|
| 2 | 7.23 | 7.11–7.35 |
| 4 | 6.72 | 6.52–6.92 |
| 6 | 7.62 | 7.43–7.81 |
| 11 | 6.37 | 6.03–6.72 |
| 17 | 6.45 | 6.20–6.79 |
| Buscopan | 6.66 | 6.54–6.78 |

The data of table 2 show that all compounds of the present invention are active, and in this respect have pA₂ values which are similar to or better than that determined for Buscopan. Of the new products, No. 6 in particular, namely endo-8-methyl-8syn-(1-methyl)-ethyl-8-azoniabicyclo-[3.2.1]-octane-3-(2-propyl)-pentanoate bromide (VAL 4000) has a spasmolytic activity 9 times better than Buscopan. This is shown by the fact that the antilogarithm of 0.96 (obtained by the difference between the two values of pA₂) is equal to 9.12.

The pharmacological investigation was therefore carried out in depth on this compound, and in order to evaluate its spasmolytic activity, the following "in vitro" and "in vivo" tests were carried out, each time in comparison with Buscopan (scopolamine-butyl-bromide) and sometimes with Papaverin.

A - "in vitro" tests
(1) Rabbit duodenum - pendular movements - (method of Magnus and coll., Pflügers Ges. Physiol., 102, 123 (1904)).
(2) Rat ileus - contraction by $BaCl_2$ (method of Magnus and coll., Pflügers Ges. Physiol., 102, 123 (1904)).
(3) Guinea-pig gall-bladder - contraction by $BaCl_2$ (Waldman D. B. and coll., Gastroenterology, 72, 932 (1977)).
(4) Total rat stomach - contraction by vagal electrical stimulation (method of Cambell G., J. Physiol., 185, 600 (1971)).
(5) Guinea-pig spiral trachea - partially contracted by carbachol (method of Costantine J. W., J. Pharm. Pharmacol., 17, 384 (1965)).
(6) Total isolated guinea-pig trachea - contraction by electrical field stimulation (method of Farmer J. B., Coleman R. A., J. Pharm. Pharmacol., 22, 46 (1970)).

B - "in vivo" tests
(1) Anesthetised cat - tonus and motality of various smooth musculature organs under various experimental conditions (method of Brock N., Lorenz D. and Bartlung H., Arch. Exper. Path. Pharmacol., 215, 512 (1952)).
(2) Anesthetised guinea-pig - intestinal loop superfused with $BaCl_2$(Brock N. and coll., Arch. Exper. Path. Pharmacol., 215, 512 (1952)).
(3) Intestinal transit in the mouse (method of Janssen P. A. and Jageneau A. H., Pharm. Pharmacol., 9, 381 (1957)).
(4) Saliva secretion in the mouse (method of Lavy U. I. and Mulder D., Arch. Int. Pharmacodyn. Ther., 178, 437 (1969)).
(5) Acute toxicity in the mouse (method of Litchfield J. T. Jr. and Wilcoxon F. A., J. Pharmac. Exp. Ther., 96, 99 (1949)).

A - "in vitro" tests
(1) Rabbit duodenum - pendular movements.

The antiperistaltic activity of VAL 4000 in comparison with Buscopan was tested at doses of between 25 and 200 ng/ml.

The compounds lead to a dose-dependent reduction in the width of the pendular movements.

In particular, VAL 4000 produces a 50% reduction at a dose of 25 ng/ml, whereas a dose four times greater (100 ng/ml) is required to obtain the same reduction with Buscopan.

In addition, for equal doses, the duration of action of VAL 4000 is about five times greater than that of Buscopan.

(2) Rat ileus - contraction by $BaCl_2$.

The direct myolytic activity of VAL 4000 was compared with that of Buscopan at doses of between 5 and 20 ng/ml and between 50 and 200 ng/ml respectively, the value of $pA_2$ being determined. VAL 4000 has a direct spasmolytic activity which is about nine times greater than that of Buscopan (see table 2).

(3) Guinea-pig gall-bladder - contraction by $BaCl_2$.

The direct spasmolytic activity of VAL 4000 was compared with that of Buscopan and Papaverin, a known direct myolytic agent, at doses of between 10 and 50 ng/ml, between 125 and 500 ng/ml and between 2500 and 7500 ng/ml respectively, by determining th $ED_{50}$ (effective dose which reduces the contractions due to $BaCl_2$ by 50%).

VAL 4000 ($ED_{50}=31$ ng/ml) was about six times more powerful than Buscopan ($ED_{50}=170$ ng/ml) and about 100 times more powerful than Papaverin ($ED_{50}=3170$ ng/ml) in inhibiting contractions induced by $BaCl_2$.

(4) Total rat stomach

The antimuscarinic activity of VAL 4000 was tested in comparison with Buscopan and Papaverin on the contractions induced by electrical stimulation of the vagus nerve, at concentrations of between 5 and 100 ng/ml, between 25 and 400 ng/ml and between 250 and 2000 ng/ml. VAL 4000 was again shown in this test to be more active than the compared drugs. In this respect, even at a concentration of 25 ng/ml, VAL 4000 showed evident antimuscarinic activity (inhibition of about 41%), whereas at this concentration Buscopan was practically inactive (inhibition of about 5%). In addition, at a concentration of 50 ng/ml, besides showing a marked antimuscarinic affect (inhibition of about 73%) of considerable duration, VAL 4000 determines a considerable reduction in the basic tonus of the organ, justified by its direct myolytic action. At a concentration of 200 ng/ml, Buscopan has only a weak antimuscarinic activity (inhibition of about 35%), whereas Papaverin shows an inhibition of about 51% only at a concentration of 2000 ng/ml.

(5) Spiral guinea-pig trachea.

The tests carried out by the cumulative dose method on prepared pieces partly contracted with carbachol (3 mcg/ml) have shown that VAL 4000 at a final concentration of 1 mcg/ml reduces the induced spasm by about 95%, whereas at the same final concentration, Buscopan was found to have poor activity (reduction of about 10% in the induced spasm) and Papaverin completely without activity (reduction of about 2%).

(6) Total isolated guinea-pig trachea.

The antimuscarinic activity of VAL 4000 was compared with Buscopan and Papaverin. When VAL 4000 is used in doses between 10 and 100 ng/ml, it antagonises the contractions of the smooth trachea muscles in a dose-dependent manner. In this range of doses, Buscopan and Papaverin are hardly active. At a concentration of 50 ng/ml, VAL 4000 produces a reduction of about 52% in the contractions, whereas at the same concentration, Buscopan reduces them by about 24% and Papaverin by about 11%.

B - "in vivo" tests
(1) Anesthetised cat
(a) urinary bladder

In order to establish a persistent musculature contraction of the organ, the animals were treated with carbachol at a dose of 50 mcg/kg subcutaneously. VAL 4000 when administered intravenously at doses of between 25 and 100 mcg/kg produces a dose-dependent spasmolytic effect. This effect proved to be considerably greater than that of Busco pan both in terms of intensity and duration of action. At intravenous doses of 50 nd 100 mcg/kg, VAL 4000 produces a drop in the pressure within the bladder of about 60 and 100 mm Hg respectively, whereas at the same doses Buscopan reduces it by about 20 and 55 mm Hg respectively. In addition to establishing a more rapid action, the duration of the effect of VAL 4000 appears much greater (about three times) than that of Buscopan. Return to the initial internal bladder pressures takes place, in the case of intravenous 50 and 100 mcg/kg doses, at 420 and 540 seconds respectively for VAL 4000, and about 140 and 228 seconds respectively for Buscopan.

(b) Stomach

The animals were treated with carbachol at a dose of 50 mcg/kg subcutaneously in order to determine activation of the smooth organ muscles such as to attain a state of hyperkinesia and hypertonia. When administered intravenously at doses of between 10 and 100 mcg/kg, VAL 4000 produces a dose-dependent spasmolytic activity which is much more powerful than that of Buscopan. For example, at a dose of 100 mcg/kg, VAL 4000 reduces the hypertonia by about 74%, whereas Buscopan reduces it by about 40%. At the same dose, VAL 4000 has a duration of action of about three times that of Buscopan.

(2) Anesthetised guinea-pig.

The tonus and intestinal motility were recorded during endoperitoneal perfusion with a Ringer-Locke solution at 37° C., medicated with $BaCl_2$ (0.33 g/l). VAL 4000, Buscopan and Papaverin were administered at various doses both intravenously and orally.

Intravenous administration: when tested at doses of between 50 and 500 mcg/kg, VAL 4000 proved to possess a dose-dependent spasmolytic activity much greater than that of Buscopan and Papaverin when tested at doses of between 250 and 2000 mcg/kg respectively. In particular, at a dose of 500 mcg/kg, VAL 4000 completely inhibits excitation of the smooth intestinal musculature promoted directly by the $BaCl_2$ (100% reduction). At the same dose, Buscopan proved to be completely inactive, and Papaverin was only poorly active (about 10% reduction).

Oral administration: in a direct comparison between VAL 4000 and Buscopan tested at doses of between 0.5 and 5 mg/kg, it was found that a dose of 5 mg/kg VAL 4000 exerts a marked spasmolytic effect (about 100% reduction) which is reater than that of Buscopan (about 45% reduction).

(3) Intestinal transit in the mouse.

The doses which inhibit the progression or transit of the opaque meal in the small intestine of the mice by 50% ($ED_{50}$) relative to the controls were determined.

| Compound | $ED_{50}$ | Reliability limits ($p = 0.05$) |
|---|---|---|
| VAL 4000 | 19 mg/kg i.m. | 11–34 |
| Buscopan | 48 mg/kg i.m. | 32–71 |

It can be seen that when administered intramuscularly, VAL 4000 has an activity of about 2.5 times greater than that of Buscopan.

The range of doses used was 7.5 to 30 mg/kg for the VAL 4000 and 30 to 60 mg/kg for the Buscopan.

(4) Saliva secretion in the mouse.

The dose necessary for inhibiting the secretagogue effect of Pilocarpine (2 mg/kg subcutaneously) by 50% ($ED_{50}$) relative to the controls was determined. VAL 4000 was compared with Atropine at doses of between 100 and 400 mcg/kg and between 15 and 100 mcg/kg respectively.

| Compound | $ED_{50}$ | Reliability limits ($p = 0.05$) |
|---|---|---|
| VAL 4000 | 190 mcg/kg s.c. | 68–532 |
| Atropine | 21 mcg/kg s.c. | 15–30 |

It can be seen that VAL 4000 has an activity ten times lower than the Atropine in inhibiting saliva secretion.

(5) Acute toxicity in the mouse

The acute toxicity of VAL 4000 in comparison with Buscopan was evaluated after intraperitoneal administration of the compounds to male mice (Swiss stock).

| Compound | $DL_{50}$ | Reliability limits ($p = 0.05$) |
|---|---|---|
| VAL 4000 | 77 mg/kg i.p. | 69.7–85.1 |
| Buscopan | 80 mg/kg i.p. | 76–84 |

In conclusion, in all the pharmacological tests carried out, VAL 4000 demonstrated a strong spasmolytic action which was constantly superior in intensity and duration of action to that of Buscopan and Papaverin. In addition, with regard to the saliva secretion, which is considered to be one of the most serious side-effects of spasmolytic agents, VAL 4000 demonstrated an inhibiting activity which was much less than that of the Atropine normally used as a reference drug for evaluating the antisialorrheic activity. Another series of pharmacological tests was carried out to evaluate the activity of VAL 4000 in comparison with its isomer Endo X. The following tests were carried out:

Isolated guinea-pig ileus (methos of Magnus and coll., Pflügers Ges. Physiol., 102, 123 (1904) ).

Rabbit duodenum - pendular movements (method of Magnus and coll., Pflügers Ges. Physiol., 102, 123 (1904) ).

Intestinal transit in the mouse (method of Janssen P.A. and Jagenau A.H., J. Pharm. Pharmacol.9, 381 (1957) ).

Acute toxicity in the mouse (method of Litchfield J.T.Jr., and Wilcoxon F.A., J. Pharmac. Exp. Ther., 96, 99 (1949) ).

(1) Isolated guinea-pig ileus

The antimuscarinic activity of VAL 4000 and Endo X, tested at doses of between 1.25 and 20 ng/ml and between 12.5 and 100 ng/ml respectively, was determined by evaluating the $pA_2$, for the definition of which reference should be made to table 2. The following values were obtained:

| Compound | $pA_2$ | Reliability limits ($p = 0.05$) |
|---|---|---|
| VAL 4000 | 8.03 | 7.82–8.24 |
| Endo X | 7.06 | 6.93–7.19 |

From these values, it can be deduced that VAL 4000 has an antimuscarinic effect which is 9.3 times greater than that of Endo X.

This is apparent by virtue of the fact that the antilogarithm of 0.97 (obtained by taking the difference between the two values of $pA_2$ calculated for the VAL 4000 and the Endo X) is equal to 9.332.

(2) Rabbit duodenum - pendular movements.

The antiperistaltic activity of VAL 4000 in comparison with Endo X, when tested at doses of between 20 and 200 ng/ml, was evaluated on the isolated rabbit duodenum. In particular, when VAL 4000 is administered at a concentration of 20 ng/ml, it produces an inhibiting effect on pendular movements (reduction of about 43%) which is greater than that caused by the same concentration of Endo X (reduction of about 17%). In addition, VAL 4000 has a duration of action which is about three times greater than that of Endo X.

(3) Intestinal transit in the mouse.

VAL 4000 and Endo X were administered intraperitoneally at doses of between 5 mg and 45 mg/kg. The effective 50% dose ($ED_{50}$) for Endo X could not be determined because even at its maximum compatible dose (45 mg/kg i.p.) in terms of its acute toxicity by intraperitoneal administration, it inhibited intestinal transit only by 32.4%. An evaluation was therefore made for both compounds of that dose which inhibits progression or transit of the opaque meal in the small mouse intestine by 25% ($ED_{25}$) with respect to the controls. The values obtained show that in a comparison between the two $ED_{25}$ values obtained, VAL 4000 is more than three times better than Endo X.

| Compound | $ED_{25}$ (mg/kg i.p.) | Reliability limits (p = 0.05) | $ED_{50}$ (mg/kg i.p.) | Reliability limits (p = 0.05) |
|---|---|---|---|---|
| VAL 4000 | 8 | 3.2–20.2 | 30 | 16.8–53.7 |
| Endo X | 25 | 9.5–66.0 | n.e. | — |

(4) Acute toxicity in the mouse.

The acute toxicity of VAL 4000 and Endo X was determined in the male mouse (Swiss stock) after intraperitoneal administration.

| Compound | $DL_{50}$ (mg/kg i.p.) | Reliability limits (p = 0.05) |
|---|---|---|
| VAL 4000 | 77 | 69.7–85.1 |
| Endo X | 62 | 50.6–75.9 |

In conclusion, it can be stated that in the pharmacological tests carried out, VAL 4000 demonstrated a spasmolytic activity which has an intensity and duration of action constantly superior and a toxicity inferior to that of Endo X, to an extent which the presence of the same functional chemical groups and the presence of the same basic structure could in no way cause one to suppose. The new compounds according to the invention can be administered orally as tablets, pills, capsules etc., parenterally in the form of phials, intramuscularly or intravenously, or rectally in the form of suppositories, diluted with the normal therapeutically acceptable excipients.

We claim:

1. Endo-8-methyl-8-syn-alkyl-8-azoniabicyclo-[3.2.1]-octane-3-alkylcarboxylate salts of formula:

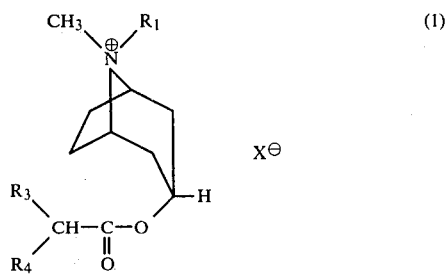

in which:
$R_1$ is a linear or branched alkyl radical of 2–5 C atoms, a cycloalkyl radical of 3–6 C atoms, or a benzyl radical
$R_3$ and $R_4$, which can be the same or different, are alkyl radicals of 1–6 C atoms
X is a halide ion.

2. Endo-8-methyl-8-syn-alkyl-8-azoniabicyclo-[3.2.1]-octane-3-alkylcarboxylate salts as claimed in claim 1, in which $R_1$ is chosen from the group consisting of ethyl, isopropyl, n-butyl, cyclohexyl and benzyl, $R_3$ and $R_4$, which can be the same or different, are chosen from the group consisting of methyl, ethyl, n-propyl, i-propyl and n-butyl, and X is Cl, Br or I.

3. The compound endo-8-methyl-8-syn-(1-methyl)-ethyl-8-azoniabicyclo-[3.2.1]-octane-3-(2-propyl)-pentanoate bromide.

4. A therapeutic composition of spasmolytic action comprising as an active ingredient an effective amount of an endo-8-methyl-8-syn-alkyl-8-azoniabicyclo-(3.2.1)-octane-3-alkylcarboxylate salt of formula:

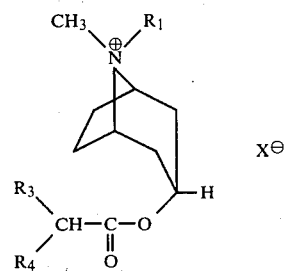

in which:
$R_1$ is a linear or branched alkyl radical of 2–5 C atoms, a cycloalkyl radical of 3–6 C atoms, or a benzyl radical,
$R_3$ and $R_4$, which can be the same or different, are alkyl radicals of 1–6 C atoms
X is a halide ion, in combination with an inert, pharmaceutically acceptable diluent, carrier or adjuvant.

5. A method of treating spasms comprising administering to a patient suffering from spasms a spasmolytically effective amount of a pharmaceutically acceptable acid addition salt of an endo-8-methyl-8-syn-alkyl-8-azoniabicyclo-(3.2.1)-octane-3-alkylcarboxylate, wherein the alkyl of 8-syn-alkyl is a linear or branched alkyl radical of 2–5 C atoms, a cycloalkyl radical of 3–6 C atoms, or a benzyl radical.

* * * * *